United States Patent
Job et al.

(10) Patent No.: US 7,888,515 B2
(45) Date of Patent: *Feb. 15, 2011

(54) METHOD FOR THE PRODUCTION OF N,N-CARBONYLDIAZOLES

(75) Inventors: Andreas Job, Köln (DE); Bernd Griehsel, Bottrop (DE); Johannes Scherer, Leverkusen (DE)

(73) Assignee: Saltigo GmbH, Leverkusen (DE)

( * ) Notice: Subject to any disclaimer, the term of this patent is extended or adjusted under 35 U.S.C. 154(b) by 532 days.

This patent is subject to a terminal disclaimer.

(21) Appl. No.: 10/583,006

(22) PCT Filed: Dec. 7, 2004

(86) PCT No.: PCT/EP2004/013876

§ 371 (c)(1),
(2), (4) Date: Feb. 2, 2007

(87) PCT Pub. No.: WO2005/063718

PCT Pub. Date: Jul. 14, 2005

(65) Prior Publication Data

US 2007/0142645 A1 Jun. 21, 2007

(30) Foreign Application Priority Data

Dec. 19, 2003 (DE) ................. 103 59 797

(51) Int. Cl.
| | |
|---|---|
| *C07D 233/58* | (2006.01) |
| *C07D 235/04* | (2006.01) |
| *C07D 249/08* | (2006.01) |
| *C07D 403/06* | (2006.01) |
| *C07D 403/08* | (2006.01) |

(52) U.S. Cl. ............. 548/305.7; 548/313.7; 548/341.5; 548/365.4

(58) Field of Classification Search ............ 548/305.7, 548/313.7, 341.5, 365.4
See application file for complete search history.

(56) References Cited

U.S. PATENT DOCUMENTS

| | | | |
|---|---|---|---|
| 6,353,115 B1 | 3/2002 | Stamm et al. | |
| 6,392,057 B1 * | 5/2002 | Scherer et al. | 548/313.7 |
| 6,465,658 B2 * | 10/2002 | Scherer et al. | 548/266.8 |
| 6,891,045 B1 * | 5/2005 | Stamm et al. | 548/313.7 |
| 7,102,012 B2 * | 9/2006 | Job et al. | 548/313.7 |

FOREIGN PATENT DOCUMENTS

| | | |
|---|---|---|
| DE | 1033210 | 7/1958 |
| EP | 0692476 | 12/1999 |
| WO | 9831672 A2 | 7/1998 |
| WO | 0001704 B1 | 1/2000 |

OTHER PUBLICATIONS

H. Staab, Liebigs Ann. Chem. 1957, 609, 75.
H. Staab, K. Wendel, Chem. Ber. 1963, 96, 3374.
Kuhn, Richard and Rewicki, Dieter, Die Lichtabsorption der Anionen hockacider Kohlenwasserstoffe, Uber hochacide Kohlenwasserstoffe, VII, Jun. 1965, pp. 50-79.
Walter, Wolfgang and Radke, Matthias, Zur Umsetzung von Azolen mit anorganischen Saurechloriden, Liebigs Ann. Chem, 1979, pp. 1756-1767.

* cited by examiner

*Primary Examiner*—Kamal A Saeed
(74) *Attorney, Agent, or Firm*—Michael A. Miller

(57) ABSTRACT

The present invention relates to an improved process for preparing N,N'-carbonyldiazoles by reacting azoles with phosgene.

14 Claims, No Drawings

METHOD FOR THE PRODUCTION OF N,N-CARBONYLDIAZOLES

The present invention relates to an improved process for preparing N,N'-carbonyldiazoles by reacting azoles with phosgene.

It is already known that N,N'-carbonyldiazoles can be obtained by reacting azoles with phosgene (see DE-B 10 33 210 and Liebigs Ann. Chem. 1957, 609, 75). In those cases tetrahydrofuran, other ethers and aliphatic or aromatic hydrocarbons are described as possible solvents; in particular, anhydrous tetrahydrofuran is used for the reaction. In that case a solution of the entire azole in the particular solvent is introduced as the initial charge, and then the phosgene is passed in. The reaction takes place at room temperature. A striking feature is the low concentration of the azole in the THF solvent, of 2% to 4% by weight. In a corresponding process, known from Chem. Ber. 1963, 96, 3374, concentrations of about 7% by weight are achieved using THF/benzene mixtures as solvents.

According to a more recent process, that of EP-A-692 476, somewhat higher concentrations of the azole in the solvent can be achieved in aromatic solvents such as benzene, toluene, xylenes, chlorobenzenes or mixtures thereof, which are each dewatered by partial distillation prior to reaction, at temperatures of 50 to 120° C. A description is given of concentrations in the range up to 12% by weight. In this case the solvent is first dewatered by partial distillation, then the azole is added and dissolved with heating, and then phosgene is passed in.

Furthermore, WO-A-00/14072 describes a process for preparing carbonyldiimidazole from imidazole and phosgene at a temperature of 60 to 80° C. which is carried out in ortho-, meta- or para-xylene, or mixtures thereof, or in chlorobenzene as solvent and in which the imidazole hydrochloride co-product obtained as a melt is separated from the resultant reaction mixture by phase separation at a temperature of more than 100° C. The reaction per se is carried out by metering phosgene into the initial charge of imidazole solution.

DE-A-198 33 913 discloses a process for preparing N,N'-carbonyldiazoles which operates using aromatic solvents such as benzene, toluene, xylene or chlorinated benzenes which are dewatered beforehand by partial distillation. A key feature is that the azole, in solution in one of the aforementioned aromatic solvents, and phosgene are metered in parallel into a further, initial charge of solvent. This type of process regime makes it possible to achieve an azole concentration of up to 33% by weight. Since, however, a fraction of the solvent used is added together with the reactants, there is no possibility here of subjecting the entire solvent volume to azeotropic drying in the vessel intended for the reaction.

Not only with the process of DE-A-198 33 913 but also with the processes described above that use aromatic solvents and run at temperatures of more than 50° C. there is a risk of the azole hydrochloride precipitate formed during the reaction being obtained as a viscous, sticky mass. This mass adheres solidly to vessel walls and stirrer, making it much more difficult to stir the system. The difficulty of the stirring operation thereby limits the maximum possible space/time yield to very low levels. In the case of solidification of the precipitate towards the end of the addition of phosgene, hard balls are formed which may, moreover, cause damage to the reaction vessel and its internals (e.g. stirrer, dip tubes, etc.).

There is therefore a need for an improved process for preparing N,N'-carbonyl-diazoles in which such tacky and problematic azole hydrochloride precipitates do not occur and, furthermore, no high reaction temperatures are needed that would reduce the economics of the process as a result of high energy costs.

The invention provides a process for preparing N,N'-carbonyldiazoles of the general formula (I)

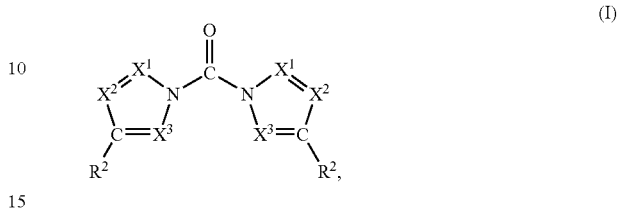

where either
$X^1$, $X^2$ and $X^3$ independently of one another are each $CR^1$ or nitrogen, $R^1$ being hydrogen or straight-chain or branched $C_1$-$C_6$ alkyl, and
$R^2$ is hydrogen, or
$X^1$ and $X^3$ are $CR^1$, the radical $R^1$ in $X^1$ being hydrogen or straight-chain or branched $C_1$-$C_6$ alkyl and the radical $R^1$ in $X^3$ forming, together with $R^2$, a —CH=CH—CH=CH— bridge, and
$X^2$ is $CR^1$ or nitrogen, $R^1$ being hydrogen or straight-chain or branched $C_1$-$C_6$ alkyl,
by reacting azoles of the general formula (II),

in which the radicals and symbols used have the definitions indicated for the general formula (I), with phosgene in a polar solvent, this process being characterized in that
(i) a polar solvent from the group consisting of ethers, ketones and chlorinated aliphatic solvents is used which possesses a maximum water content of 0.5% by weight, and
(ii) in that the azole of the general formula (II) and also the phosgene are metered into this solvent in such a way that in the time within which 1 mol of azole of the general formula (II) is metered in at the same time 0.17 to 0.34 mol of phosgene is metered in.

In the process of the invention, in contrast to the process described in DE-A-198 33 913, the azole hydrochloride which precipitates during the reaction, such as the imidazole hydrochloride, for example, is formed and remains continually as a readily stirrable, crystalline precipitate which does not cake or stick to stirrer or vessel walls. Owing to the disperse nature of the precipitate, the stirring resistance is much lower than in the case of a non-inventive mode of operation. In accordance with the invention it is therefore possible to use significantly higher reactant concentrations than hitherto, which results in a significantly improved space/time yield as compared with the prior art. In the process of DE-A-198 33 913 a reactant concentration of 28% to 33% by weight is reported, whereas with the process of the invention reactant concentrations, for example, of more than 40% by weight, and hence considerably improved space/time yields, are obtained. It is also possible to rule out damage to the reactor and its internals as a result of hard azole hydrochloride conglomerates.

Furthermore, the process of the invention exhibits very slight sensitivity to overphosgenation, which in other processes leads to discoloration of the isolated product.

In the process of the invention it is possible to use either two different azoles or else only one single azole of the general formula (II). In the first case an N,N'-carbonyldiazole of the formula (I) is obtained in which the two azole rings are different. In the second case an N,N'-carbonyldiazole with two identical azole rings is formed. This second procedural variant is the preferred variant.

Preference is further given to using azoles in which in the general formulae (I) and (II) one or two of the moieties $X^1$, $X^2$ and $X^3$ is or are nitrogen. Additionally it is preferred for $X^1$ to be CH, $X^2$ to be nitrogen and $X^3$ to be $CR^1$, $R^1$ and $R^2$ together forming a —CH=CH—CH=CH— bridge.

Particular preference is given to using, in the process of the invention, imidazole, benzimidazole, pyrazole or 1,2,4-triazole as the azole of the general formula (II). Very particular preference is given to imidazole.

The said azoles of the general formula (I) are either available commercially or else are preparable by known processes of the prior art.

Phosgene can be used in its usual technical quality. It is advantageous to make use in total, per mol of azole of the general formula (II), of 0.2 to 0.3 mol, preferably 0.22 to 0.27 mol, in particular 0.24 to 0.26 mol of phosgene.

The polar solvent to be used must come from the group consisting of ethers, ketones and chlorinated aliphatic solvents.

Ethers employed include, for example, linear or cyclic aliphatic ethers and diethers, especially MTBE, dimethyl ether, diethyl ether, dibutyl ether, THF, 2-methyl-THF, 2,5-dimethyl-THF, dioxane, ethylene glycol dimethyl ether or ethylene glycol diethyl ether, aromatic ethers, especially anisole and chlorinated derivatives of anisole, and also mixtures of the aforementioned solvents.

Ketones which can be used include, for example, linear or cyclic aliphatic ketones, especially acetone, 2-butanone, diethyl ketone, dipropyl ketone, cyclopentanone, cyclohexanone or cycloheptanone, and also mixtures of the aforementioned solvents.

Chlorinated aliphatic solvents which can be used include, for example, methylene chloride, chloroform and 1,2-dichloroethane.

The polar solvent from the abovementioned group that is used possesses a water content of not more than 0.5% by weight, preferably of not more than 0.2% by weight, more preferably of not more than 0.1% by weight and in particular of not more than 0.05% by weight. Solvents with this water content are available either commercially or else by corresponding partial distillation/drying.

The azole of the general formula (II) that is used can be metered in the form of a solution or a suspension in the aforementioned solvents, this solution or suspension suitably possessing a temperature in the range from 20 to 100° C., preferably 40 to 80° C., or as a melt. This kind of metering facilitates the control of the metering rate.

The process of the invention is typically carried out at a temperature in the range from 20 to 100° C., preferably at 40 to 80° C., in particular at 40 to 65° C.

It is an essential feature of the process of the invention that the azole of the general formula (II) and also the phosgene are metered in simultaneously with the polar solvent from the group consisting of ethers, ketones and chlorinated aliphatic solvents, in such a way that in the time within which 1 mol of azole of the general formula (II) is metered in at the same time 0.17 to 0.34 mol, preferably 0.2 to 0.3 mol, in particular 0.24 to 0.28 mol of phosgene is metered in.

In this context it is possible to adopt a procedure such that first of all exclusively a certain amount of the polar solvent is charged to the reaction vessel, and the azole and also phosgene are metered in as specified above.

In a further, preferred embodiment the reaction vessel is charged with up to 10% by weight, preferably 0.1% to 2% by weight, of the total amount of the azole, in the form of a solution or suspension, in the reaction vessel, and subsequently the further amount of the azole, and the phosgene, are metered in simultaneously as specified. This procedure makes it possible to prevent phosgene being present in a significant molar excess with respect to the azole (molar phosgene:azole ratio=0.3 or higher) at the beginning of the reaction. Such molar ratios favor decomposition of the azole with accompanying darkening of the reaction mixture.

In general it is advantageous, after the reactants have been simultaneously metered in, to stir the reaction mixture at the same temperature for a time in the range from 30 minutes to 5 hours.

The reaction mixture is worked up by slurrying it from the reaction vessel into a filtration apparatus. Since the azole hydrochloride is in the form of a crystalline precipitate even after the end of the metered addition of azole of the formula (II) and phosgene, this slurrying is easy and complete. Then the azole hydrochloride precipitate formed is separated off by filtration at 20 to 100° C., preferably at 40 to 80° C. This filtration as well, owing to the crystalline consistency of the precipitate, is accomplished effectively and within short filtration times. The N,N'-carbonyldiazole can be isolated from the mother liquor obtained during the azole hydrochloride separation by cooling the mother liquor to +40 to −70° C., preferably to +25 to −20° C., and filtering off the product which crystallizes out in the course of cooling. In this way the product is obtained in a well-crystallized form in purities of at least 90%, preferably at least 95%.

It is also possible to concentrate the mother liquor to completion following the azole hydrochloride separation and so to free it from the solvent. The N,N'-carbonyldiazole obtained in this way likewise possesses a purity of at least 90%, preferably of at least 95%.

Half of the azole used in the process according to the invention is obtained as azole hydrochloride. This can be converted back into the free azole and so recycled to the reaction. In this way it is possible to achieve a doubling in the yield of N,N'-carbonyldiazole, based on the azole employed.

The recovery of azoles from azole hydrochlorides can be carried out in accordance with DE-A-198 33 913, for example, by reacting the azole hydrochlorides obtained in the synthesis of the N,N'-carbonyldiazoles with a compound of the formula (III)

$$M(OR^4)_n \qquad \qquad (III),$$

in which n corresponds to the valency of M,

M is an alkali metal or alkaline earth metal and $R^4$ is hydrogen or $C_1$-$C_4$ alkyl.

This reaction takes place in a solvent mixture composed on the one hand of an aromatic solvent such as, for example, benzene, toluene, a xylene, monochloro-benzene, a dichlorobenzene, a trichlorobenzene or mixtures thereof and, on the other hand, of a solvent of the formula

R⁴OH  (IV), in which
R⁴ has the definition indicated with respect to formula (III).

In the formulae (III) and (IV) R⁴ is preferably hydrogen or methyl, and in formula (III) M is preferably lithium, sodium or potassium.

After the reaction of the azole hydrochloride with the compound of the formula (III) it is advantageous to distil off the entire compound of the formula (IV), including the compound of the formula (IV) formed during the reaction of azole hydrochloride and the compound of the formula (III), to remove the resulting salt $MCl_n$ by filtration at normal or elevated temperature, and to use the azole recovered, following separation of the aromatic solvent, for the N,N'-carbonyldiazole synthesis of the invention.

This procedure goes particularly well if the compound of the formula (III) used is LiOH, NaOH or KOH in a solvent mixture composed of water (which is a compound of the formula (IV) with R⁴=hydrogen) and chlorobenzene, toluene, xylene or 2-methyltetrahydrofuran and if the water is removed by azeotropic distillation, for example, by separating it off on a water separator, or else, if the compound of the formula (III) used is sodium methoxide in a solvent mixture composed of methanol on the one hand and of chlorobenzene or xylene on the other, and if the methanol is separated off by distillation, by, for example, distilling it from the mixture via an effective column.

In summary it is possible with the process of the invention, through the parallel metering of azole and phosgene using a polar solvent from the group consisting of ethers, ketones and chlorinated aliphatic solvents, to produce the azole hydrochloride obtained as by-product reliably in a non-tacky consistency. This allows the stirring properties of the reaction solution to be improved and hence allows higher concentrations of reactants and correspondingly higher space/time yields to be achieved. At the same time the easy removal of the azo hydrochloride from the reaction vessel is ensured, and damage due to hardened azo hydrochlorides is ruled out. The filtration times as well are surprisingly short by virtue of the improved filtration characteristics of the azole hydrochloride. A further advantage of the inventive use of a polar solvent is the very low sensitivity of the reaction system to any excess of phosgene during or at the end of the reaction: as compared with prior art processes, both the consistency of the crystalline azole hydrochloride precipitate and the colour of the N,N'-carbonyldiazole obtained from the reaction mixture are affected little if at all by small excesses of phosgene.

EXAMPLES

Example 1

Inventive

A flask is charged with 120 g of dry THF, which is heated to 60° C. 33 ml of a solution, heated at 62° C., of 250 g of imidazole and 165 g of dry THF are metered into the reaction vessel. Thereafter at 60° C. the remainder of the aforementioned solution is metered in at a uniform rate over 1.75 h, at a rate of 216 g/h, and, simultaneously, 96 g of phosgene are metered in as well, at a rate of 55 g/h, into the reaction system.

Subsequently, the imidazole solution feedline is rinsed with 40 g of THF, the rinse solution being transferred likewise into the reaction flask. The mixture is subsequently stirred at 60° C. for 1.5 h. In order to ensure a phosgene-free reaction mixture, 19 g of solvent are distilled off at 750 mbar and 55° C. and discarded. The imidazole hydrochloride by-product (isolated dry weight: 209 g) is removed by filtration at 60° C., the filter cake being washed with 100 g of THF which has been heated to 60° C. The solvent is removed from the combined filtrates at 45° C. and 20 mbar. This gives 130 g of carbonylbisimidazole with a purity of 98.2%, corresponding to a yield of 86% of theory.

Example 2

Comparative

A flask is charged with 250 g of imidazole in 285 g of dry THF. The mixture is heated to 60° C. At this temperature, 92 g of phosgene are metered into the flask at a rate of 55 g/h. At this point a suspension is obtained which is so thick that only parts of the reaction mixture are still mixed by the stirrer. The experiment must therefore be discontinued at this point, and the contents of the flask discarded.

Example 3

Inventive

A flask is charged with 218 g of dry acetone, which is heated to 45° C. 20 ml of a solution, heated at 47° C., of 125 g of imidazole and 120 g of dry acetone are metered into the reaction vessel. Thereafter at 45° C. the remainder of the aforementioned imidazole solution is metered in at a uniform rate over 1.75 h, at a rate of 132 g/h, and, simultaneously, 48 g of phosgene are metered in as well, at a rate of 28 g/h, into the flask. Subsequently, the imidazole solution feedline is rinsed with 30 g of acetone, the rinse solution being transferred likewise into the reaction flask. The mixture is subsequently stirred at 45° C. for 1.5 h.

In order to ensure a phosgene-free reaction mixture, 19 g of solvent are distilled off at 770 mbar and 45° C. and discarded.

The imidazole hydrochloride by-product (isolated dry weight: 102 g) is removed by filtration at 45° C., the filter cake being washed with 50 g of acetone which has been heated to 45° C.

The combined filtrates are cooled to 0° C. and stirred at this temperature for 30 minutes. The carbonylbisimidazole which precipitates is separated off by filtration, the precipitate being additionally displaced with 30 g of acetone that has been cooled to 0° C.

Drying of the precipitate at 45° C. and 20 mbar yields 53.7 g of carbonylbisimidazole with a purity of 97.5%, corresponding to a yield of 71% of theory.

Example 4

Inventive

A flask is charged with 120 g of dry THF, which is heated to 60° C. 8 ml of a solution, heated at 62° C., of 250 g of imidazole and 165 g of dry THF are metered into the reaction vessel. Thereafter at 60° C. the remainder of the aforementioned imidazole solution is metered in at a uniform rate over 1.75 h, at a rate of 234 g/h, and, simultaneously, 91 g of phosgene are metered in as well, at a rate of 52 g/h, into the flask. Subsequently, the imidazole solution feedline is rinsed with 40 g of THF, the rinse solution being transferred likewise into the reaction flask. The mixture is subsequently stirred at 60° C. for 1.5 h.

In order to ensure a phosgene-free reaction mixture, 17 g of solvent are distilled off at 750 mbar and 55° C. and discarded.

The imidazole hydrochloride by-product (isolated dry weight: 185 g) is removed by filtration at 60° C., the filter cake being washed with 100 g of THF which has been heated to 60° C.

The combined filtrates are cooled to 0° C. and stirred at this temperature for 30 minutes. The carbonylbisimidazole which precipitates is separated off by filtration, the precipitate being additionally displaced with 50 g of THF that has been cooled to 0° C.

Drying of the precipitate at 45° C. and 20 mbar yields 107 g of carbonylbisimidazole with a purity of 92.8%, corresponding to a yield of 67% of theory.

The invention claimed is:

1. A process for preparing a N,N'-carbonyldiazole of formula (I)

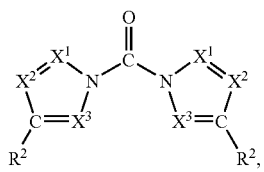

where either
- $X^1$, $X^2$ and $X^3$ independently of one another are each $CR^1$ or nitrogen, $R^1$ being hydrogen or straight-chain or branched $C_1$-$C_6$ alkyl, and
- $R^2$ is hydrogen, or
- $X^1$ and $X^3$ are $CR^1$, the radical $R^1$ in $X^1$ being hydrogen or straight-chain or branched $C_1$-$C_6$ alkyl and the radical $R^1$ in $X^3$ forming, together with $R^2$, a —CH=CH—CH=CH— bridge, and
- $X^2$ is $CR^1$ or nitrogen, $R^1$ being hydrogen or straight-chain or branched $C_1$-$C_6$ alkyl, by reacting azoles of the general formula (II),

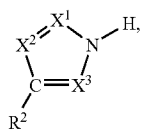

wherein $X^1$, $X^2$, $X^3$, and $R^2$ are as defined for formula (I) with phosgene in a polar solvent, which is characterized in that
(i) the polar solvent being selected from the group consisting of ethers, ketones and chlorinated aliphatic solvents, wherein the polar solvent possesses a maximum water content of 0.5% by weight, and
(ii) the azole of the general formula (II) and the phosgene are metered into the solvent in such a way that in the time within which 1 mol of azole of the general formula (II) is metered in at the same time 0.17 to 0.34 mol of phosgene is metered in.

2. Process according to claim 1, characterized in that either two different azoles or else only one single azole of the general formula (II) are or is used.

3. Process according to claim 1, characterized in that one or two azoles of the general formula (II) is or are used in which independently of one another one or two of the moieties $X^1$, $X^2$ and $X^3$ is or are nitrogen.

4. Process according to claim 1, characterized in that one or two azoles of the general formula (II) is or are used in which independently of one another $X^1$ is CH, $X^2$ is nitrogen and $X^3$ is $CR^1$, $R^1$ and $R^2$ together forming a —CH=CH—CH=CH— bridge.

5. Process according to claim 1, characterized in that imidazole, benzimidazole, pyrazole or 1,2,4-triazole is used as the azole of the general formula (II).

6. Process according to claim 1, characterized in that in total 0.2 to 0.3 mol, preferably 0.22 to 0.27 mol, in particular 0.24 to 0.26 mol of phosgene is used per mole of azole of the general formula (II).

7. Process according to claim 1, characterized in that ethers used are linear or cyclic aliphatic ethers and diethers, especially MTBE, dimethyl ether, diethyl ether, dibutyl ether, THF, 2-methyl-THF, 2,5-dimethyl-THF, dioxane, ethylene glycol dimethyl ether or ethylene glycol diethyl ether, aromatic ethers, especially anisole and chlorinated derivatives of anisole, and also mixtures of the aforementioned solvents.

8. Process according to claim 1, characterized in that ketones used are linear or cyclic aliphatic ketones, especially acetone, 2-butanone, diethyl ketone, dipropyl ketone, cyclopentanone, cyclohexanone or cycloheptanone, and also mixtures of the aforementioned solvents.

9. Process according to claim 1, characterized in that chlorinated aliphatic solvents used are methylene chloride, chloroform or 1,2-dichloroethane.

10. Process according to claim 1, characterized in that the polar solvent possesses a water content of not more than 0.2%, preferably 0.1% and in particular 0.05% by weight.

11. Process according to claim 1, characterized in that the azole of the general formula (II) and also the phosgene are metered in simultaneously to the polar solvent from the group consisting of ethers, ketones and chlorinated aliphatic solvents is such a way that in the time within which 1 mol of azole of the general formula (II) is metered in at the same time 0.2 to 0.3 mol, in particular 0.24 to 0.28 mol, of phosgene is metered in.

12. Process according to claim 1, characterized in that the reaction vessel is charged with up to 10% by weight, preferably 0.1% to 2% by weight, of the total amount of the azole of the general formula (II), in the form of a solution or suspension, in the reaction vessel, and subsequently the further amount of the azole, and the phosgene, are metered in simultaneously as specified in claims 1 and 10.

13. Process according to claim 1, characterized in that the reaction mixture is worked up by separating off the azole hydrochloride precipitate at 20 to 100° C., preferably 40 to 80° C., by filtration and isolating N,N'-carbonyldiazole from the filtrate by cooling the mother liquor to +40 to −70° C., preferably to +25 to −20° C., and filtering off the product that crystallizes out in the course of cooling.

14. Process according to claim 1, characterized in that the reaction mixture is worked up by separating off the azole hydrochloride precipitate at 40 to 80° C. by filtration as indicated in claim 13 and concentrating the filtrate completely and thereby removing the solvent.

* * * * *